United States Patent
Castillo et al.

(10) Patent No.: US 8,369,920 B2
(45) Date of Patent: Feb. 5, 2013

(54) MUCOSAL SENSOR ADAPTOR

(75) Inventors: Carlos Castillo, Palm Springs, CA (US); Max Harry Weil, Rancho Mirage, CA (US); Joe Bisera, Camarillo, CA (US); Clayton Young, Palm Springs, CA (US)

(73) Assignee: Institute of Critical Care Medicine, Rancho Mirage, CA (US)

( * ) Notice: Subject to any disclaimer, the term of this patent is extended or adjusted under 35 U.S.C. 154(b) by 1906 days.

(21) Appl. No.: 10/860,829

(22) Filed: Jun. 4, 2004

(65) Prior Publication Data

US 2005/0203362 A1 Sep. 15, 2005

Related U.S. Application Data

(60) Provisional application No. 60/551,546, filed on Mar. 9, 2004.

(51) Int. Cl.
*A61B 5/05* (2006.01)
(52) U.S. Cl. .......................... 600/349; 600/353
(58) Field of Classification Search .................. 600/353, 600/323, 322, 354, 309, 301, 344, 350, 587, 600/529, 532; 422/84; 128/124.1, 126.1, 128/201.26, 206.29
See application file for complete search history.

(56) References Cited

U.S. PATENT DOCUMENTS

| | | | |
|---|---|---|---|
| 5,109,849 A * | 5/1992 | Goodman et al. | 600/483 |
| 5,511,546 A * | 4/1996 | Hon | 600/490 |
| 5,579,763 A | 12/1996 | Weil et al. | |
| 5,665,477 A * | 9/1997 | Meathrel et al. | 428/500 |
| 5,800,349 A * | 9/1998 | Isaacson et al. | 600/323 |
| 6,055,447 A * | 4/2000 | Weil et al. | 600/353 |
| 6,071,237 A * | 6/2000 | Weil et al. | 600/309 |
| 6,216,024 B1 * | 4/2001 | Weil et al. | 600/353 |
| 6,258,046 B1 * | 7/2001 | Kimball et al. | 600/593 |
| 6,285,899 B1 * | 9/2001 | Ghaem et al. | 600/391 |
| 6,411,834 B1 * | 6/2002 | Nagai | 600/348 |
| 7,127,278 B2 * | 10/2006 | Melker et al. | 600/340 |
| 2001/0009265 A1 * | 7/2001 | Schulz et al. | 250/227.14 |
| 2001/0029324 A1 * | 10/2001 | Walker et al. | 600/323 |
| 2001/0045532 A1 * | 11/2001 | Schulz et al. | 250/559.4 |
| 2002/0028990 A1 * | 3/2002 | Shepherd et al. | 600/340 |
| 2003/0162414 A1 * | 8/2003 | Schulz et al. | 439/11 |
| 2003/0225324 A1 * | 12/2003 | Anderson et al. | 600/364 |
| 2003/0236452 A1 * | 12/2003 | Melker et al. | 600/323 |
| 2004/0006263 A1 * | 1/2004 | Anderson et al. | 600/364 |
| 2004/0054291 A1 * | 3/2004 | Schulz et al. | 600/500 |
| 2004/0230108 A1 * | 11/2004 | Melker et al. | 600/340 |
| 2004/0260161 A1 * | 12/2004 | Melker et al. | 600/340 |
| 2005/0085704 A1 * | 4/2005 | Schulz et al. | 600/344 |
| 2007/0027375 A1 * | 2/2007 | Melker et al. | 600/340 |
| 2007/0078307 A1 * | 4/2007 | Debreczeny et al. | 600/309 |
| 2007/0078317 A1 * | 4/2007 | Matlock | 600/323 |
| 2007/0078318 A1 * | 4/2007 | Kling et al. | 600/323 |
| 2007/0106168 A1 * | 5/2007 | O'Neil et al. | 600/532 |

* cited by examiner

*Primary Examiner* — Michael Kahelin
*Assistant Examiner* — Michael R Bloch
(74) *Attorney, Agent, or Firm* — Leon D. Rosen

(57) ABSTRACT

Devices for treating a patient by measuring a condition, such as the partial pressure of $CO_2$, at a location on a mucosal membrane surface in the mouth region of the patient, includes a sensor (14, 16) with an end (44, 46) that lies against the mucosal surface, and a seal (20) that extends 360° around the sensor end and presses against the mucosal surface. The sensor end and the seal lie on the first end portion (24) of a holder (22) which has a second end portion (26) that presses against the outside of the patient at a location opposite the sensor and seal. The holder is a clasp which can be formed as a single piece of resilient material that extends in a loop, or which can be formed in the manner of a clothespin with a spring that pivots two bars to urge their end portions towards each other.

1 Claim, 3 Drawing Sheets

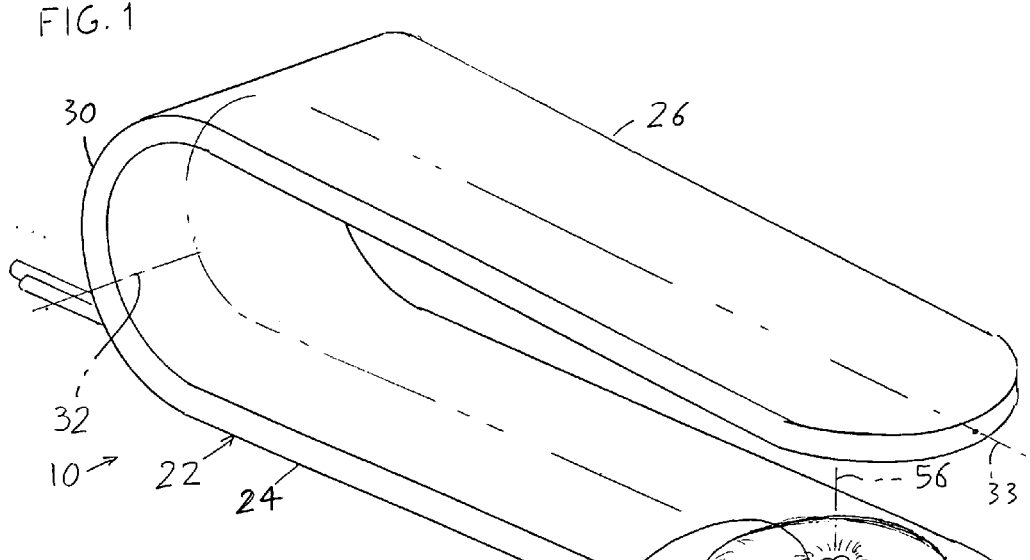
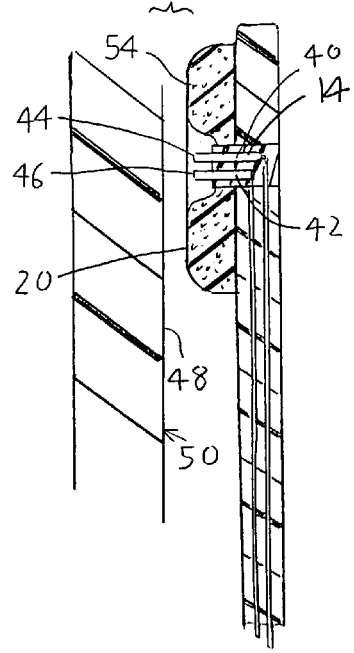
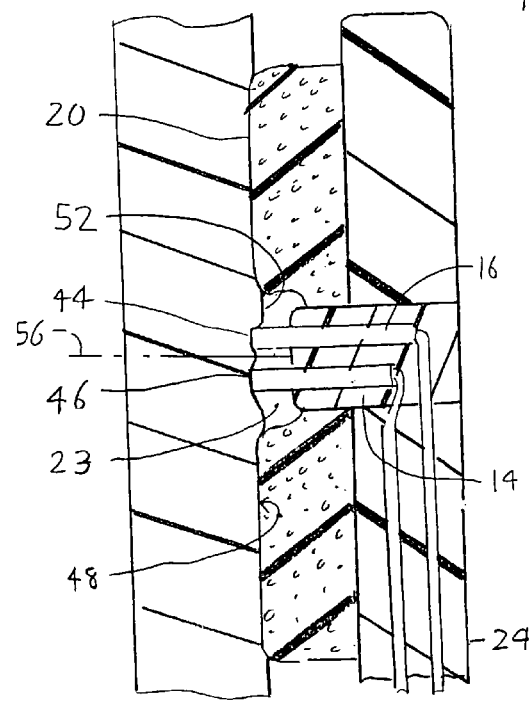

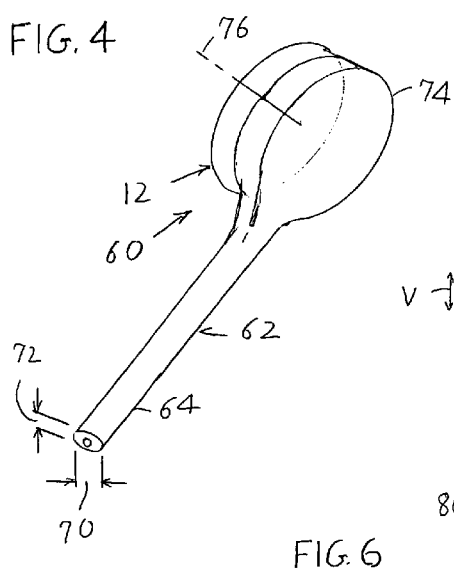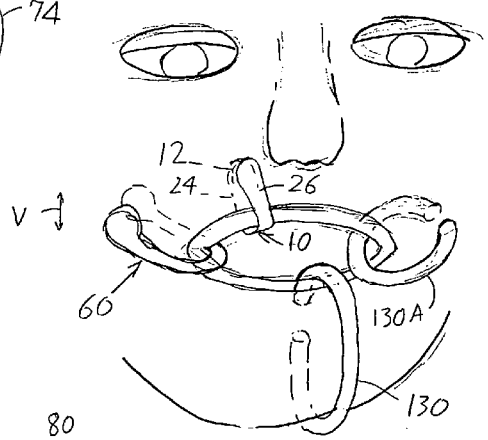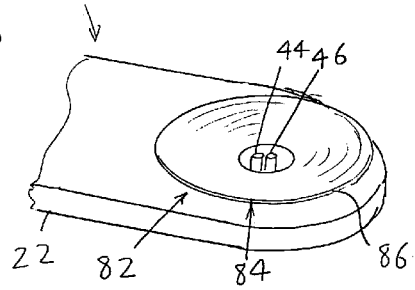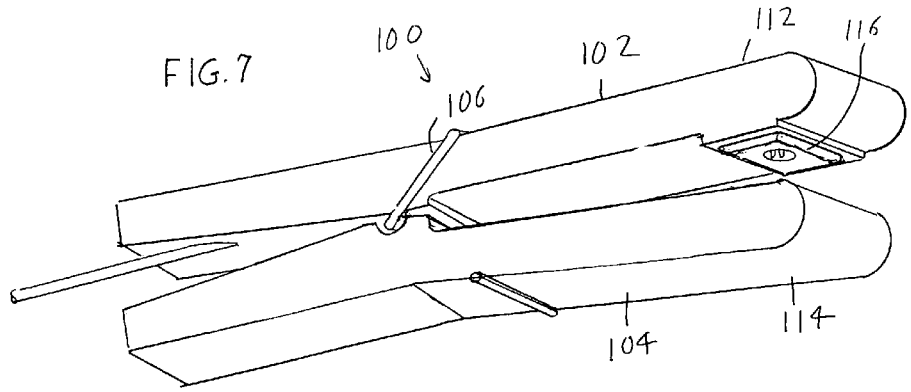

MUCOSAL SENSOR ADAPTOR

CROSS REFERENCE

Applicant claims priority from U.S. provisional application 60/551,546 filed Mar. 9, 2004.

BACKGROUND OF THE INVENTION

The measurement of $CO_2$ in tissues (cells) of a patient who is in a critical condition, such as a heart attack or bleeding patient being resuscitated, is a good indicator of the effectiveness of blood circulation in the patient. In our earlier U.S. Pat. Nos. 5,579,763 and 6,055,447 we described the measurement of $CO_2$ by placing a sensor against mucosal tissue under the tongue, and sealing the volume under the tongue to prevent air flow that would carry away $CO_2$ and therefore affect $CO_2$ measurements. This required a person, such as a caregiver, to hold the apparatus in place. If a region immediately around the location where a $CO_2$ sensor was in contact with a mucosal surface could be reliably sealed, without requiring a caregiver to continually hold the apparatus in place with his/her hand, this would provide more reliable measurements of $CO_2$, temperature or other measurable conditions of the patient and free the caregiver to perform other tasks.

SUMMARY OF THE INVENTION

In accordance with one embodiment of the invention, a sensor apparatus is provided that can be easily applied to a patient to hold a sensor, such as a $CO_2$ sensor, against a location on the surface of mucosal tissue in the mouth area of the patient; the apparatus is constructed to not only hold the sensor in place, but to continually seal a region immediately around the sensor, without requiring manual holding of any part. The apparatus comprises a sensor arrangement that includes a sensor end with an axis that extends normal (perpendicular) to the sensed location of the mucosal surface. The sensor arrangement also includes a seal that extends 360° around the sensor end. The seal is preferably of elastomeric material.

A holder that holds the sensor arrangement against the mucosal surface, continually applies a spring force to the sensor arrangement that presses the sensor arrangement against the mucosal surface with a controlled force. The holder is preferably a clasp with first and second end portions that are resiliently biased towards each other. The sensor arrangement is mounted on the first end portion of the clasp. The first end portion with the sensor arrangement mounted thereon is inserted into the mouth of the patient and placed against a location on mucosal tissue in the mouth, while the second end portion lies outside the patient's mouth and presses thereagainst.

One form of holder includes a curved rod of resilient material that extends in a loop. Another form of holder includes a pair of rods forming the first and second end portions, and a spring that biases the rod end portions towards each other, the sensor arrangement being mounted on one of the rod end portions.

The novel features of the invention are set forth with particularity in the appended claims. The invention will be best understood from the following description when read in conjunction with the accompanying drawings.

BRIEF DESCRIPTION OF THE DRAWINGS

FIG. 1 is an isometric view of a mucosal tissue sensing apparatus of a first embodiment of the invention, wherein the holder is a clasp that extends in about a 180° loop.

FIG. 2 is a partial sectional view of a cheek of a patient and of a portion of the apparatus of FIG. 1 prior to installation on the mouth region of the patient.

FIG. 3 is an enlarged view of a portion of the patient's cheek and the apparatus of FIG. 2 fully installed on the patient.

FIG. 4 is a partial sectional isometric view of mucosal tissue sensing apparatus of another embodiment of the invention wherein the holder transforms in cross section to more easily fit between the lips of the patient.

FIG. 5 is an isometric view of the apparatus of FIG. 4 and other apparatus, shown installed on a patient.

FIG. 6 is a partial isometric view of apparatus similar to that of FIG. 1 except that the seal is in the form of a suction cup.

FIG. 7 is an isometric view of apparatus of another embodiment of the invention wherein the holder is in the general form of a clothespin.

DESCRIPTION OF THE PREFERRED EMBODIMENTS

Figure 8:
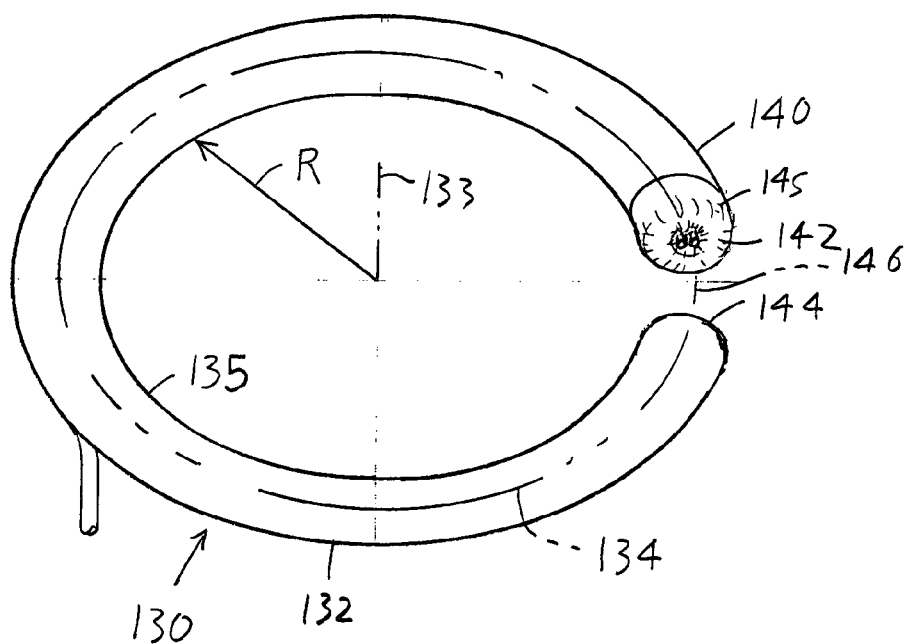
FIG. 8 is an isometric view of apparatus of another embodiment of the invention wherein the holder is formed of a curved bar extending in about a 360° loop.

FIG. 1 illustrates an apparatus 10 for taking measurements at the surface of mucosal tissue in the mouth region of a patient. The apparatus comprises a sensor arrangement 12 that includes sensors 14 with sensor end portions 16 that can engage a mucosal surface (surface of mucosal tissue) in the mouth region of the patient, and a seal 20 extending around the sensor end portions. A holder 22 holds the sensor arrangement 12 so the sensor end portions engage the mucosal surface, while the seal 20 seals the microenvironment 23 lying immediately around the sensor arrangement and within a hollow in the seal.

The holder 22 shown in FIG. 1 is a clasp comprising a bar of resilient material (elastomeric or not) extending in about a 180° loop. The clasp 22 has first and second opposite end portions 24, 26 and a middle portion 30 that connects them. The end portions are substantially straight while the middle portion forms the 180° loop around a loop axis 32. The bar has a bar axis 33. The seal 20 is in the form of a donut of elastomeric material (material with a Young's modulus of elasticity of no more that 50,000 psi). As shown in FIG. 2, the sensors 14 comprise a $CO_2$ sensor 40 and a temperature sensor 42. The end portions of the sensors have tips 44, 46 that should contact the surface 48 of mucosal tissue 50 of the patient, in order to obtain accurate readings of the $CO_2$ partial pressure in the patient's tissue and to measure the temperature of the patient's body. It is possible for the seal 20 to be integral with the clasp 22, but the seal can be herein referred to separately.

FIG. 3 shows the sensor tips 44, 46 engaged with a location 52 on the mucosal tissue, with the seal 20 pressed against the mucosal tissue around the location 52. The seal extends completely around the location, or in other words 360° around the location 52, to prevent air circulation though the microenvironment 23 that lies within the seal. Any such air circulation would carry away some of the $CO_2$ and cool the tissue location, resulting in inaccurate $CO_2$ and temperature measurements. The sensor arrangement has an axis 56 that extends normal (perpendicular) to the tissue surface 48, and the seal extends in a 360° around the axis.

Applicant prefers to position the sensor tips 44, 46 so they are slightly recessed from the outer surface 54 of the undeformed elastomeric seal 20, as shown in FIG. 2. The sensor arrangement presses with a force such as 100 grams against the mucosal tissue. This results in the elastomeric seal, which may be a soft resilient foam, being compressed while the sensor tips 44, 46 press against the mucosal surface. As shown in FIG. 5, the second end portion 26 of the clasp 22 presses against the outside of the body in the mouth region, opposite the sensor arrangement 12, the particular location shown being on an upper portion of the cheek of the patient. It is possible to use a seal of rigid material, in which case the sensor tips are close to being flush with the seal surface.

FIG. 4 shows a modified mucosal tissue sensing apparatus 60 wherein the clasp 62 has a cross-section that changes along its length. The seal axis 76 is horizontal so the clasp 62 extends horizontally and through the patient's lips. At the middle portion 64 of the clasp, the cross-section has a horizontal width 70 that is at least as great as its vertical thickness 72, to fit between the lips of the patient while enabling easy closing of the lips, as when oxygen is being administered. However, at the first end portion 24 where the sensor arrangement 12 is located, the clasp has a greater vertical V thickness (if the patient were standing) and the same or smaller horizontal width to hold a sensor arrangement of appreciable seal diameter. This construction facilitates mounting the apparatus 60 as shown in FIG. 5 wherein the clasp extends largely horizontally (with respect to the patient if he/she were standing).

FIG. 6 illustrates a portion of an apparatus 80 wherein the clasp type holder 22 is of the same construction as in FIG. 1, but the sensor arrangement 82 is different. The sensor arrangement 82 includes a suction cup 84 for the seal. The tips 44, 46 of the sensor end portions are recessed deeper with respect to the rim 86 of the suction cup, to enable compression of the suction cup and slight expansion to form a vacuum to hold it in place. This construction is generally not preferred because it requires pressing the end portions of the clasp together with a higher force (e.g. 200 grams) and releasing the force to form a vacuum in the suction cup, and because the depression of the sensor tips into the mucosal tissue is more difficult to predict.

FIG. 7 illustrates a modified apparatus 100 wherein the clasp is in the general form of a clothespin. That is, the clasp includes first and second end portions 102, 104 in the form of largely straight bars, and a spring 106 that urges the far ends 112, 114 of the end portions towards each other. A sensor arrangement 116 lies on the first far end 112. The first bar at 102 can be constructed with a portion of reduced width to better fit between the lips of the patient.

Figure 9:
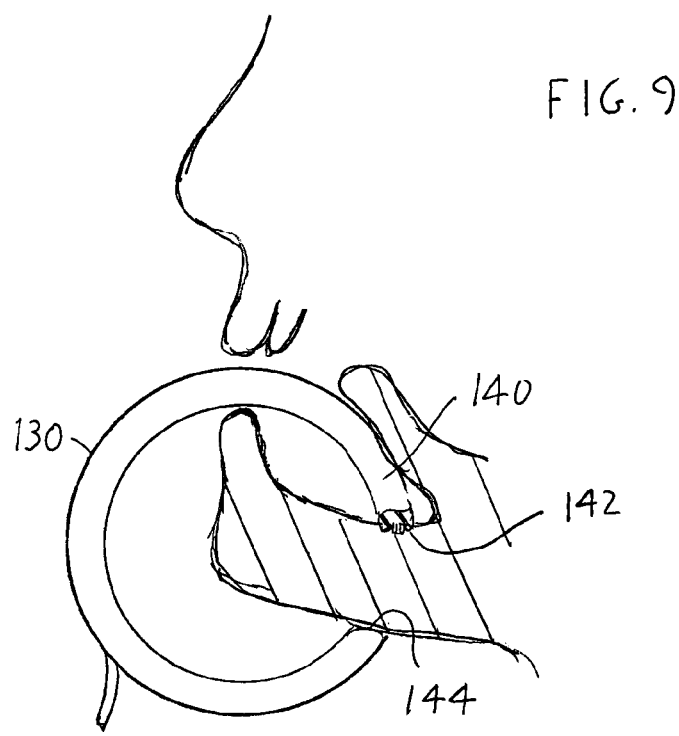
FIG. 9 is a sectional view of a portion of a patient, with the apparatus of FIG. 8 installed thereon.

FIG. 8 illustrates a modified apparatus 130 in which the clasp 132 is in the form of a bar of resilient material that is bent in a loop 135 of about 360° about a loop axis 133. The bar has an axis 134 that extends along the center of the length of the bent bar, this axis also extending in about a 360° loop. The radius of curvature R of the bend is at least about 2 centimeters and preferably no more than 7 centimeters, so the clasp can fit around the chin of the patient, as shown in FIG. 9 without being cumbersome, with the first end portion 140 that bears a sensor arrangement 142 lying against sublingual mucosal tissue (tissue under the patient's tongue). The second end portion 144 lies against the outside of the body, against the under-chin of the patient. The apparatus 130 also can be placed against the cheek, as shown at 130A in FIG. 5. The seal 145 of the sensor arrangement can be formed by the end of the bar, or by a separate part as shown in FIG. 8.

Applicant notes that in FIG. 8, the axis 146 of the sensor arrangement is about parallel to the curved axis 134 of the curved bar, at the first end of the bar. In the apparatus 10 of FIG. 1, the seal axis 56 at the part of the seal that engages the mucosal surface, is perpendicular to the length of the first clasp end portion 24.

Thus, the invention provides apparatus for measuring a characteristic of a patient, such as the partial pressure of $CO_2$ and/or the temperature of the patient, by one or more sensors that press against mucosal tissue in the mouth region of the patient. The apparatus includes a holder that holds a sensor, and a seal that extends 360° around the sensor, and that continually presses the sensor and seal against a mucosal surface location. The holder comprises a clasp with first and second end portions that are pressed towards each other. The second end portion presses against the outside of the patient while the first end portion, which carries the seal and sensor, presses them against the mucosal surface at the inside of the patient's mouth. One clasp is formed by a bar of resilient material that has a portion that extends in about a 180° loop and is especially useful for a sensor that presses against the cheek area. Another clasp is formed by a bar of resilient material that extends in about a 360° loop and is especially useful to press against a mucosal surface location that lies under the tongue although it can be applied to the cheek. Another clasp is in the general form of a clothespin. The seal is preferably formed by a ring (or square) of elastomeric material, but can be a suction cup.

Although particular embodiments of the invention have been described and illustrated herein, it is recognized that modifications and variations may readily occur to those skilled in the art, and consequently, it is intended that the claims be interpreted to cover such modifications and equivalents.

What is claimed is:

1. A mucosal tissue sensing apparatus which includes a sensor arrangement and a holder for holding the sensor arrangement at a mucosal surface of mucosal tissue in the mouth region of a patient, wherein:

said sensor arrangement includes a sensor with a sensor end, a seal that has a seal axis, said seal extending 360° around said axis and forming a hollow microenvironment within said seal, said sensor lying in said microenvironment, said seal being constructed of a material chosen from the group of materials that consist of elastomeric and rigid materials;

said seal having a sealing surface that faces generally in a first direction along said seal axis to seal to the mucosal surface of the patient;

said holder is constructed to apply a spring force that continually presses said seal and presses said sensor end, firmly toward the mucosal surface;

said sensor end being positioned to lie against the mucosal surface within said 360° when said holder presses said seal against the mucosal surface, to thereby hold the sensor end against a location on the mucosal surface while sealing the area immediately around the location;

said holder comprises a clasp in the form of a bar that is bent in about a primarily 360° loop to form first and second end portions that face each other, said loop being large enough to fit around the patient's jaw so said first end portion can press against a location under the patient's tongue while the second end portion can press against an under-chin area on the outside skin of the patient or said end portions can press against the cheek of the patient.

* * * * *